United States Patent [19]
Dishman et al.

[11] Patent Number: 5,260,666
[45] Date of Patent: Nov. 9, 1993

[54] CAPACITANCE MONITOR FOR SOIL MOISTURE

[75] Inventors: Michael R. Dishman; Alfred W. Jordan, both of Raleigh, N.C.

[73] Assignee: Troxler Electronic Laboratories, Inc., Research Triangle Park, N.C.

[21] Appl. No.: 763,917

[22] Filed: Sep. 23, 1991

[51] Int. Cl.⁵ .................................. G01R 27/26
[52] U.S. Cl. ................................ 324/664; 324/690
[58] Field of Search ............ 324/664, 690, 366, 220; 340/602; 73/73; 361/78; 137/392; 33/304, 544, 542, 542.1

[56] References Cited

U.S. PATENT DOCUMENTS

| | | | |
|---|---|---|---|
| 3,279,249 | 10/1966 | Tocanne | 324/664 |
| 3,437,924 | 4/1969 | Tocanne | |
| 3,780,442 | 12/1973 | Gresho | 33/542 |
| 4,876,506 | 10/1989 | Brown et al. | 324/220 |
| 4,929,885 | 5/1990 | Dishman | 324/664 |
| 4,952,868 | 8/1990 | Scherer, III | 324/690 |

FOREIGN PATENT DOCUMENTS

| | | |
|---|---|---|
| 3237594 | 4/1984 | Fed. Rep. of Germany . |
| 2210693 | 6/1989 | United Kingdom . |
| WO86/05278 | 9/1986 | World Int. Prop. O. . |

*Primary Examiner*—Kenneth A. Wieder
*Assistant Examiner*—Maura K. Regan
*Attorney, Agent, or Firm*—Bell, Seltzer, Park & Gibson

[57] ABSTRACT

A capacitance monitor for monitoring the moisture content of soil is disclosed in which a capacitance sensing probe having a generally cylindrical probe body and an elongate tubular handle is inserted into an access tube to measure the capacitance of the soil and to thereby determine the moisture content of the soil. The cylindrical probe body has aluminum electrodes separated by a polypropylene dielectric spacer and two sets of circumferentially spaced apart spring biased stainless steel plungers that extend radially outwardly from the probe body to engage the side wall of the access tube and to center the probe body within the access tube. The two sets of plungers are located at opposite ends of the probe body. The capacitance monitor also includes a top cap assembly mounted on the extreme upper end portion of the access tube that includes a cover plate having beveled side walls to engage the spring biased plungers on the probe body to urge the spring biased plungers radially inwardly for easy insertion of the probe body into the access tube. The top cap assembly also includes a stop assembly means for engaging circumferential grooves on the tubular handle to control reproducibly positioning the probe body at predetermined depths within the access tube.

28 Claims, 3 Drawing Sheets

CAPACITANCE MONITOR FOR SOIL MOISTURE

FIELD OF THE INVENTION

This invention is directed to a capacitance monitor for determining soil moisture content in which a capacitance sensing probe is inserted into an access tube embedded in the soil to measure the moisture content of the soil. More particularly, the present invention relates to a probe having improved centering within the access tube.

BACKGROUND OF THE INVENTION

Capacitance monitors are well known for determining the moisture content of soil and have a variety of applications. Capacitance monitors have been used to optimize irrigation schedules to conserve precious water resources and to study the movement of water through soils. For example, capacitance monitors are useful for determining moisture penetration under a road bed or around a hazardous waste site.

An example of a moisture sensing probe for use in soils is described in U.S. Pat. No. 4,929,885. The patented probe provides direct contact with the soil and has a tapered probe body that improves contact between the surrounding soil and the electrodes of the probe.

Another type of capacitance monitor, in which the capacitance sensing probe is designed for insertion into an access tube that is embedded in the soil, is disclosed in Bell, J. P., T. J. Dean and M. G. Hodnett, *Soil Moisture Measurement By An Improved Capacitance Technique*, parts I, II, Journal of Hydrology, 93 (1987): 67–78, 79–90. In this system, a number of access tubes can be installed in a field and the capacitance sensing probe can be inserted successively into different access tubes to determine a moisture profile for an entire field. The accuracy of the profile depends on precise installation of the access tube and on precisely reproducing the position of the probe body within the access tube.

The disclosed probe body is fitted with a polyvinyl chloride ("PVC") extension tube of the same diameter as the probe. A mounting block fitted to the top of the access tube holds a spring loaded key that is said to provide reproducible depth positions by engaging a series of indents spaced along the extension tube. Fabric centralizing rings spaced along the access tube engage the probe as it is moved axially within the access tube to center the probe within the access tube.

However, precise and reproducible radial positioning of a probe within an access tube is critical to obtain accurate results in measuring soil moisture content. The fabric centralizing ring does not always center the probe body with precision and does not take account of variations in the diameter of the access tubes that result from the tolerances with which such tubes are formed or variations from the tolerances themselves.

With the foregoing in mind, it is an object of the present invention to overcome the limitations of the prior capacitance monitors discussed above and to provide a capacitance monitor for determining soil moisture content in which a capacitance sensing probe is inserted into an access tube embedded in the soil with precise and reproducible radial and axial positioning to provide more accurate measurement of soil moisture.

SUMMARY OF THE INVENTION

The above and other objects of the invention have been achieved in accordance with the present invention by a capacitance monitor that insures the precise and reproducible radial and axial positioning of a probe body within an access tube. In accordance with the present invention, an access tube is embedded in the soil and a capacitance sensing probe is inserted into the access tube for measuring the moisture content of the soil. More specifically, the capacitance sensing probe includes a generally cylindrical probe body that has at least one pair of electrodes separated by a dielectric spacer. The electrodes are substantially rigid structural components that form a portion of the probe body. At least one of the structural components has an electronic circuit located within an internal cavity. The probe body also includes at least two sets of a circumferentially spaced apart plurality of means that extend radially outwardly from the probe body and engage the side wall of the access tube to center the probe body within the tube. The two sets of means are longitudinally spaced along the probe body. The means for engaging the side wall of the access tube insures that the probe body is precisely centered within the access tube, despite small variations in the inner diameter of the access tube.

In a more specific embodiment, the means for engaging the side wall of the access tube includes projecting surfaces, such as at least three equidistant and circumferentially spaced spring biased plungers. In a still more specific and preferred embodiment, the spring biased plungers may be formed of stainless steel cylinders having rounded outer end portions that project radially outwardly from the probe body. A compression spring engages the inner end portion of the stainless steel plunger to urge the plunger cylinder radially outwardly from the probe body. Two sets of these circumferentially spaced and spring-biased plungers are located at opposite ends of the probe body.

In a still more specific embodiment, the capacitance sensing probe of the invention also includes an elongate tubular handle of a smaller diameter than the probe body, which may be formed from PVC pipe. The handle can be mounted on the probe body by a variety of means, and facilitates axially moving the probe body within the access tube. One preferred means is to thread the handle onto a threaded end cap on one end of the probe body.

Yet even more specifically, the capacitance monitor includes in addition to the capacitance sensing probe a top cap assembly mounted over the opening of the access tube that provides a stop assembly means to engage the tubular handle on the probe body to control reproducibly positioning the probe body at a predetermined depth within the access tube. The top cap assembly also provides an aperture for insertion of the probe body into the access tube. The aperture has beveled side walls for engaging the first and second sets of plunger means on the probe body and urges them radially inwardly so that the probe body can be inserted into the access tube.

BRIEF DESCRIPTION OF THE DRAWINGS

Some of the features and advantages of the invention have been stated, and others will become apparent as the description of the invention proceeds, taken into conjunction with the accompanying drawings, in which.

DESCRIPTION OF THE PREFERRED EMBODIMENT

The present invention will now be described more fully, with reference to the drawings, in connection with a particular embodiment of the capacitance monitor for soil irrigation. This invention can, however, be used within other contexts for measuring the moisture content of a sample by capacitance determination. It should be understood, therefore, that the specific embodiment described herein is an illustration of how the present invention may be practiced, and that the invention is not limited to this specific embodiment.

Figures 1, 2:
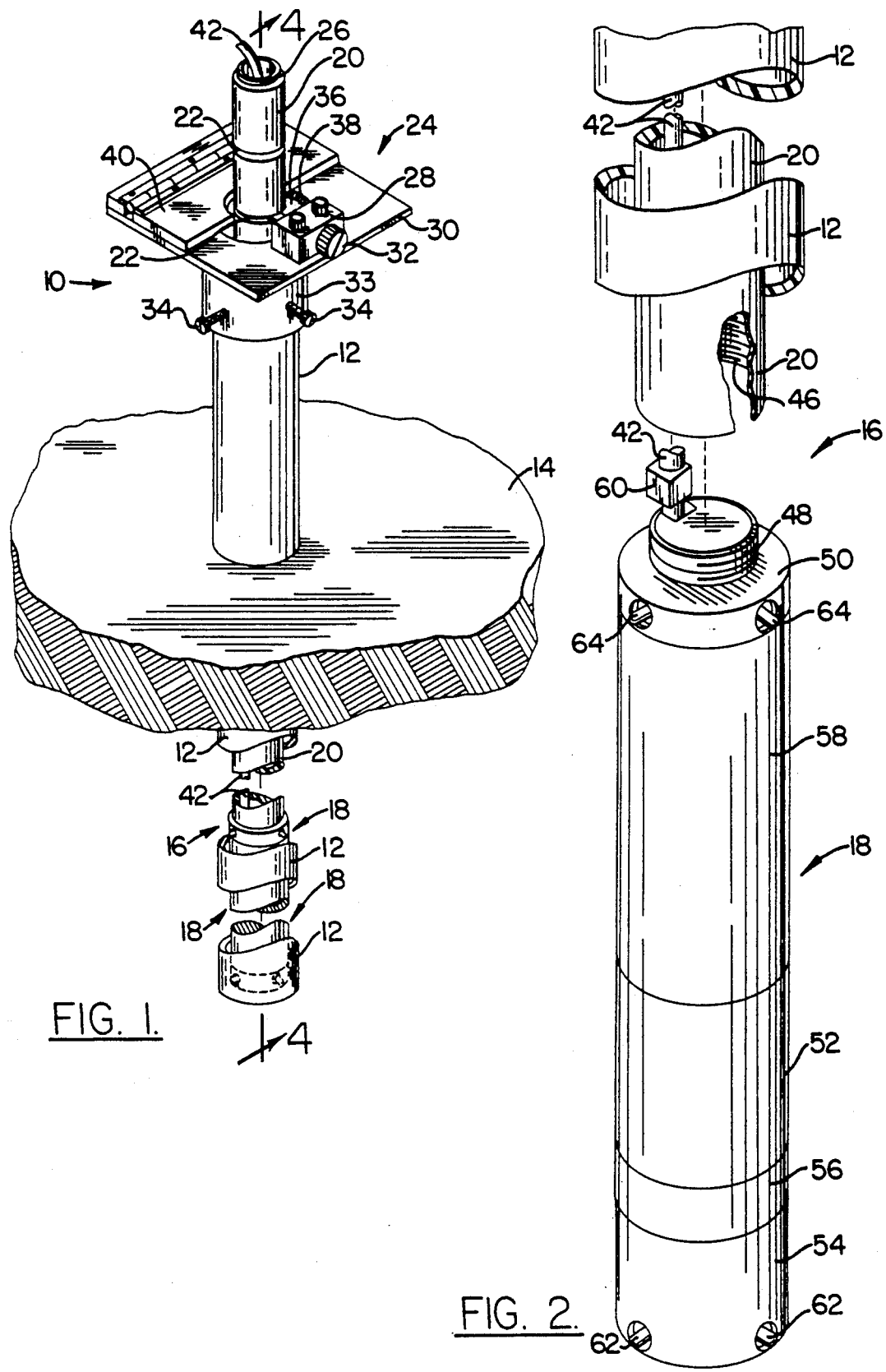
FIG. 1 is a perspective view of a preferred embodiment of the capacitance monitor of the present invention.
FIG. 2 is a perspective view of the probe body and tubular handle of the capacitance sensing probe of the present invention.

A capacitance monitor for monitoring soil irrigation is generally identified in FIG. 1 by the numeral 10. An access tube 12 (shown more clearly in FIG. 4) provides access to the soil 14 for a capacitance sensing probe 16, which is illustrated more clearly in FIG. 2. Access tube 12 is preferably made of PVC pipe so that the pipe will be readily available, durable, resist corrosion, and at the same time not interfere with capacitance measurement. Access tube 12 extends below the level of the soil as shown and defines the full depth to which a capacitance sensing probe 16 can be inserted.

Access tube 12 should be precisely installed to avoid introducing gaps between the tube and the soil, as is described in the aforementioned Bell, J. P., T. J. Dean and M. G. Hodnett, *Soil Moisture Measurement By An Improved Capacitance Technique*, parts I, II, Journal of Hydrology, 93 (1987): 67-78, 79-90, which is incorporated herein by reference.

Capacitance sensing probe 16 has two primary parts: 1) a cylindrical probe body that is shown generally at 18 for monitoring soil moisture, which is described more fully hereinbelow, and 2) elongate tubular handle 20. Elongate tubular handle 20 facilitates axially moving probe body 18 within access tube 12 and includes a plurality of circumferential grooves 22 that cooperate with a top cap assembly 24 in a manner hereinafter described to control reproducibly positioning the probe body 18 at predetermined depths within the access tube 12. Handle 20 is preferably formed of threaded sections of PVC pipe having threaded end portions 26 that can be joined to form handles of varying lengths and is of smaller diameter than the probe body 18.

To control reproducibly positioning the probe body 18 at predetermined depths, top cap assembly 24 includes a stop assembly means 28 mounted on a cover plate 30. The stop assembly means 28 includes a spring biased stop pin 32 mounted for engagement with a plurality of circumferential grooves 22 in tubular handle 20. The cover plate 30, on which is mounted the stop assembly 28, is in turn fixedly mounted to a top cap assembly sleeve 33 that fits over the end of access tube 12. The top cap assembly sleeve 33 is mounted on the access tube 12 by circumferentially spaced means such as radially adjustable screws 34 for engaging the wall of the access tube 12.

Probe body 18 and tubular handle 20 enter the access tube through aperture 36 in cover plate 30 that is disposed over the opening of the access tube 12. Aperture 36 is sized to receive the probe body 18 into the access tube 12. Aperture 36 is provided with a beveled edge 38 to facilitate inserting the probe body into the access tube, as will be described hereinbelow. When the tubular handle is of smaller diameter than the aperture, then the cover plate includes a hinge plate 40 that is hingeably mounted to the cover plate 30 for reducing the size of aperture 36 when the probe body 18 is in the access tube 12 and the smaller diameter handle 20 extends through aperture 36 for engagement with stop means 28.

The capacitance signal is carried by a coaxial cable 42, which is shown exiting tubular handle 20. Coaxial cable 42 is connected at one end to the probe body 18 (as shown in FIG. 2) and at the opposite end to a control box 44 that is above the ground (as shown in FIG. 4).

FIG. 2 illustrates the external details of the capacitance sensing probe of the present invention, which is illustrated generally by the number 16, and which include the probe body 18 and elongate tubular handle 20. The elongate tubular handle 20 has a threaded internal portion 46 for engaging a threaded portion 48 of end cap 50 of probe body 18. Probe body 18 is further shown as having structural members 52 and 54 which comprise electrically conductive capacitance sensing electrodes. These electrodes are right circular cylinders preferably formed of aluminum to provide good conduction and to resist corrosion. A dielectric spacer 56, which is preferably polypropylene, is securely attached to each of the electrodes 52 and 54 so that the electrodes are dielectrically and longitudinally spaced apart at opposite ends of the spacer 56. Optionally, probe body 18 also includes a tubular sleeve 58 of dielectric material between the end cap 50 and electrode 52 to facilitate handling of the probe body.

Coaxial cable 42 exits the probe body 18 through the end cap 50 and carries the electrical signal generated by the interaction of the soil and electrodes. Coaxial cable 42 includes a ferrite shield 60 to substantially reduce undesirable signal interference, such as capacitative coupling between the outer conductor of the coaxial cable and electrode 54.

Figures 4, 5:
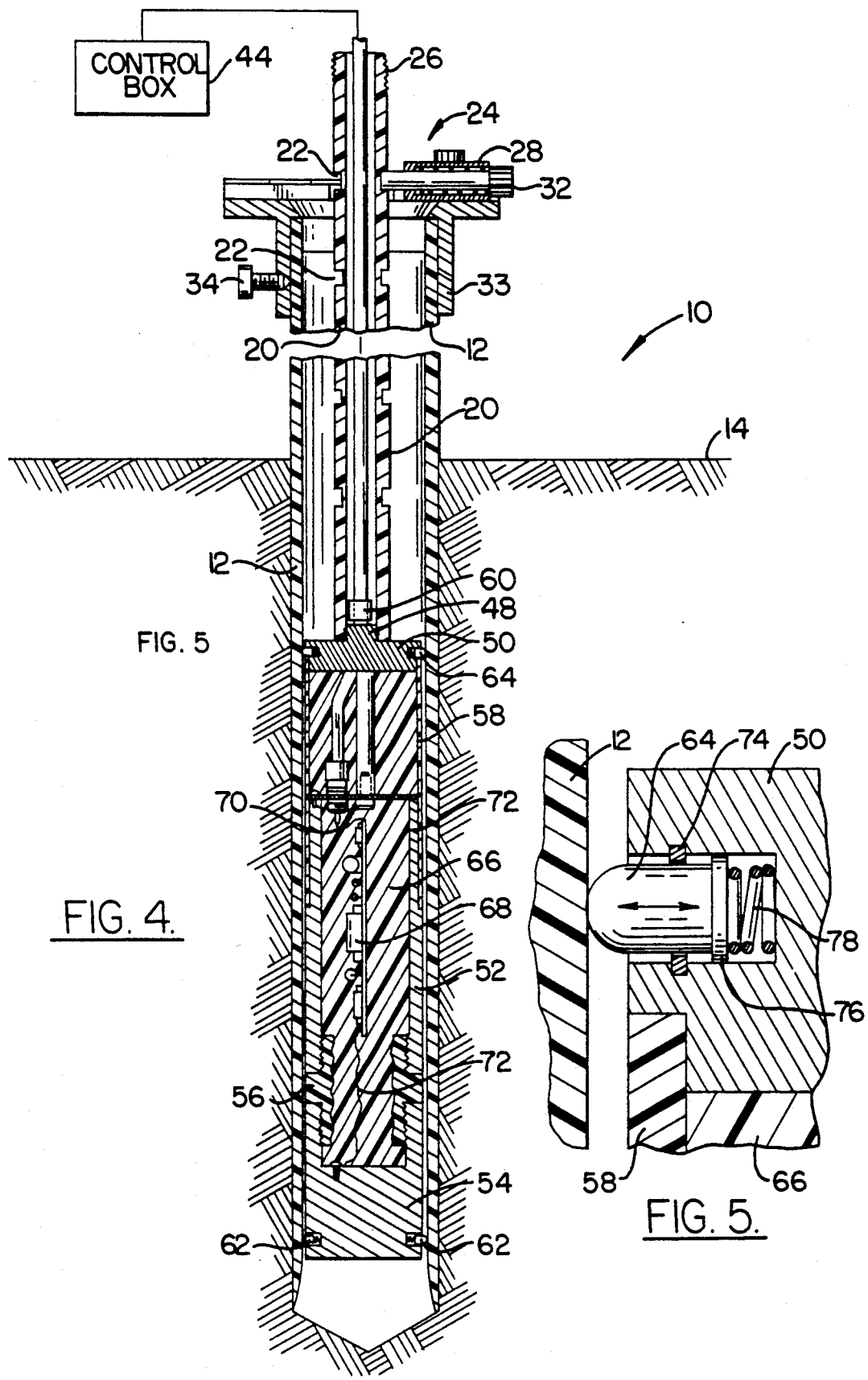
FIG. 4 is a cross section view of the capacitance monitor of the present invention.
FIG. 5 is an enlarged partial cross section view of a portion of the capacitance monitor of FIG. 4.

Electrode 54 includes a circumferentially spaced apart plurality of means 62 extending radially outwardly from the probe body for engaging the side wall of the access tube 12 (as shown in FIG. 4) and centering the probe body 18 within the tube. End cap 50 also includes an analogous circumferentially spaced apart plurality of means 64 that extend radially outwardly from the probe body 18 for engaging the side wall of the access tube 12 and centering the probe body 18 within the access tube 12. Means 62 and 64 are located at opposite ends of the probe body 18. Each set of means 62 and 64 preferably comprise spring biased plungers that are formed of stainless steel cylinders having rounded outer end portions that project radially outwardly from the probe body.

Figure 3:
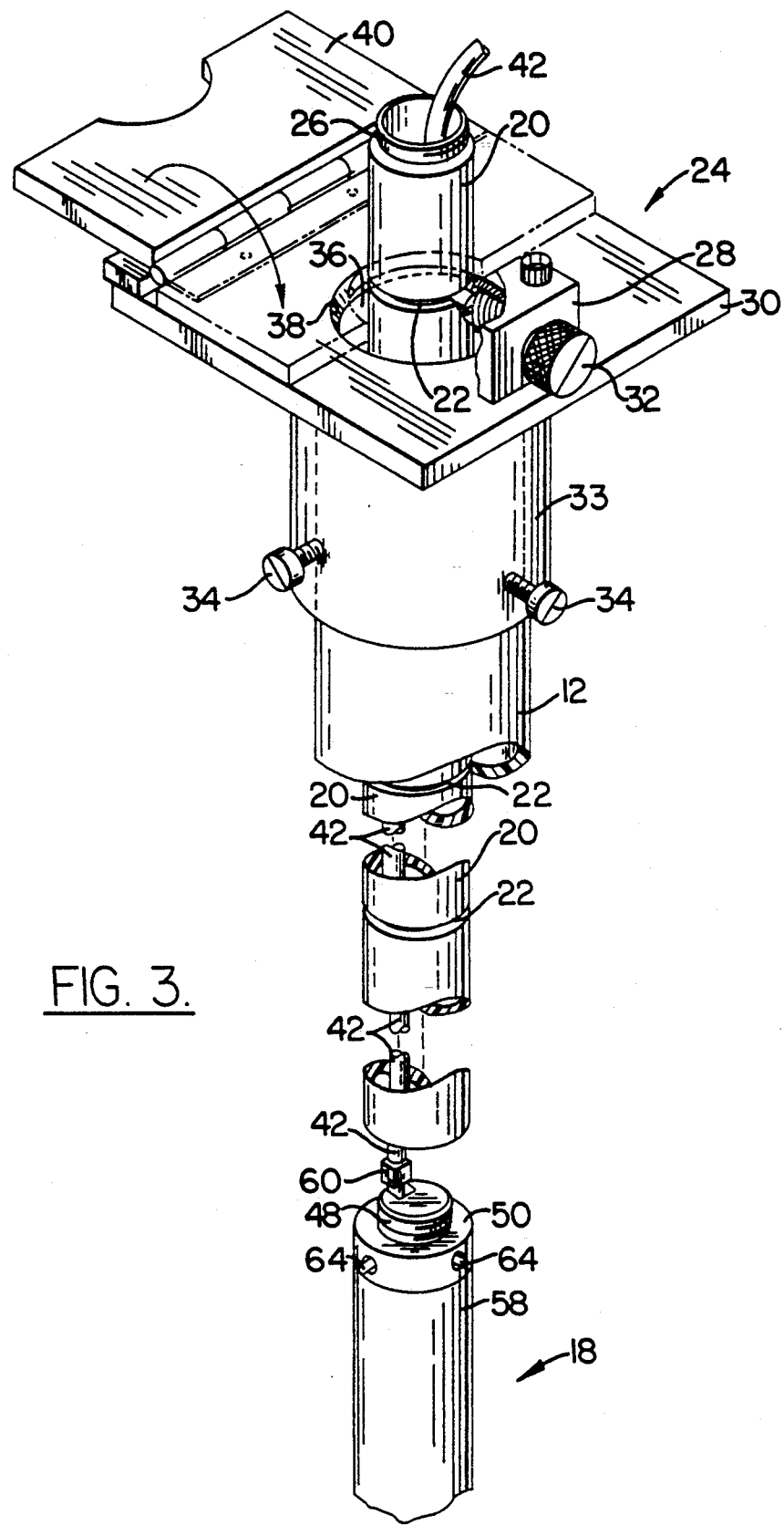
FIG. 3 is a perspective view showing the details of the top cap assembly of the present invention.

Turning now to FIG. 3, FIG. 3 illustrates the details of the top cap assembly 24 and shows a partially broken away view of spring biased pin 32 of stop assembly 24 in engagement with circumferential grooves 22 of tubular handle 20 for reproducibly positioning the probe body 18 at a predetermined depth within the access tube 12. Hinge plate 40 is shown closed in phantom to provide a smaller aperture for abutment of tubular handle 20 to support the handle against engagement of spring biased stop pin 32.

Beveled side walls 38 of aperture 36 in cover plate 30 provide a means for engaging the plungers 62, 64 on the probe body 18 and urging them radially inwardly so that the probe body 18 can easily be inserted in the access tube 12.

Turning now to FIG. 4, FIG. 4 illustrates the internal details of the capacitance monitor 10 of the present invention in longitudinal section and shows an internal cavity contained within probe body 18 that has been filled with a dielectric filler 66 to prevent moisture damage to electrical circuit 68 that is contained within the internal cavity. Electrical circuit 68 is electrically connected to each of electrodes 52 and 54 through wires 70 and 72, respectively. In the illustrated embodiment, the upper portion of the probe formed by the tubular sleeve 58 is attached to the upper end of electrode 52 by an adhesive or other means. The tubular sleeve 58 is a right circular cylinder as are the electrodes 52 and 54 and is of the same diameter as the electrodes. The tubular portion 58 is preferably formed of a resilient dielectric material such as fiberglass. End cap 50 is attached to the end of the probe body 18, which is the upper end of the tubular sleeve 58, by an adhesive or other means. The end cap includes a threaded portion 48 that may form an integral part of the end cap 50 or may be attached by any suitable conventional means. A handle 20 is shown threaded about the threaded portion 48 of the end cap 50.

In accordance with the preferred embodiment of the present invention, the moisture content of the soil is determined by measuring the capacitance of the soil. The dielectric constant for most soils is between two and four. Water, however, has a dielectric constant of approximately 78 to 81 depending on the temperature. Therefore, the capacitance of the soil provides a good indication of the moisture content of the soil.

The capacitance monitor 10 is provided with an LC circuit that includes electrode 52, electrical connection wires 70 and 72, control box 44, and second electrode 54. The circuit board 68 includes an oscillator having a particular resonant frequency in the range of 50 MHz. A change in the capacitance of the soil in the proximity of the electrodes causes a shift to the resonant frequency which can be easily measured by the control box 44. The probe electrodes 52 and 54 are periodically briefly switched out of the circuit by means of switching circuitry on the circuit board 68 during which time a reference frequency is determined, and the frequency shift is measured relative to this reference frequency. The control box 44 provides an indication of the moisture content of the soil to the user by correlating the capacitance of the soil to the moisture content of the soil. Correlation is developed by successively measuring various known test samples and recording the measured capacitances. The data may then be correlated by any known method, such as a mathematical formula or simply by maintaining an array of the various capacitances cross-referenced with the appropriate moisture contents.

Of particular importance is the moisture impermeability of the internal cavity formed within the probe body 18. To seal the cavity, the spacer 56 is tightly coupled to the electrodes 52 and 54 by threaded end portions that sealingly resist penetration of water. The tubular sleeve portion 58 is sealed to the second electrode 52 over the extended shoulder portion 72 and the top cap 50 is sealed to the tubular portion 58. To further assure that the cavity is sealed, the internal cavity is back-filled with dielectric filler 66. The dielectric filler 66 also fixes the circuit board 68 and wires 70 and 72 in place and provides a further moisture barrier against corroding or damaging the circuit board 68.

Turning now to FIG. 5, FIG. 5 illustrates in partial section an enlarged portion of FIG. 4 showing how stainless steel plungers 64, which are in the form of cylinders and have a rounded outer end portion, projecting radially outwardly from the probe body 18 to engage the side wall of the access tube 12 to center the probe. Cylinder 64 is shown embedded in an aperture in the end cap 50 and having sealing means 74 to engage a rear portion 76 of the plunger cylinder that is of larger diameter and prevents the plunger from falling out of the aperture. A spring 78 located radially inwardly of the plunger biases the plunger 64 against the end cap 50 in a radially outward position to engage the side wall of the access tube 12. Plungers 64 are analogous and are placed in apertures formed in electrode 54, as shown in FIG. 4.

In an alternative embodiment according to the present invention, the probe includes a thin protective coating. For example, the probe may have a thin coating of ceramic or plastic or other nonconductive material to provide a smooth outer surface that will resist the scratches and abrasions the probe receives without affecting the accuracy of the measurements.

The foregoing description is to be considered illustrative rather than restrictive of the invention, and those modifications that come within the meaning and range of equivalents of the claims are to be included therein.

What is claimed is:

1. A capacitance sensing probe for measuring the moisture content of soil through an access tube embedded in the soil, said capacitance sensing probe having a generally cylindrical body comprising:
   first and second substantially rigid structural components formed of aluminum and shaped as right circular cylinders and defining, respectively, first and second electrically conductive capacitance sensing electrodes;
   a dielectric spacer formed of polypropylene and shaped on a right circular cylinder securely attached to each of said first and second structural components such that said components are dielectrically and longitudinally spaced apart at opposite ends of said spacer;
   an internal cavity formed within at least one of said structural components;
   an electronic circuit located within said internal cavity and electrically connected to each of said first and second electrodes;
   a first circumferentially spaced apart plurality of means extending radially outwardly from said probe body for engaging the side wall of the access tube and centering said probe body within the tube; and
   a second circumferentially spaced apart plurality of means extending radially outwardly from said probe body for engaging the side wall of the access tube and centering said probe body within the tube, said second means being longitudinally spaced from said first means.

2. The capacitance sensing probe of claim 1 wherein said first and second plurality of means for centering said probe body within the access tube comprise projecting surfaces for engaging the side wall of the tube.

3. The capacitance sensing probe of claim 2 wherein said projecting surfaces of each of said first and second means comprise at least three equidistant and circumferentially spaced plungers and corresponding compression springs for biasing said plungers radially outwardly from said probe body to engage the sidewall of the access tube.

4. The capacitance sensing probe of claim 3 wherein said spring biased plungers are formed of stainless steel cylinders having a rounded outer end portion that projects radially outwardly from said probe body and having an inner end portion engaging said compression spring, said compression spring urging said plunger cylinder radially outwardly from said probe body.

5. The capacitance sensing probe of claim 1 wherein said first and second plurality of means for centering said generally cylindrical probe body within the access tube are located at opposite ends of said probe body.

6. The capacitance sensing probe of claim 1 including an elongate tubular handle and means for mounting said handle to one end of said cylindrical probe body to facilitate axially moving said probe body within the access tube.

7. The capacitance sensing probe of claim 6 wherein said means for mounting said handle on said probe body comprises a threaded end cap on one end of said probe body and a corresponding threaded portion on said tubular handle.

8. The capacitance sensing probe of claim 7 wherein said handle is of smaller diameter than said probe body and is formed from PVC pipe.

9. The capacitance sensing probe of claim 6 wherein said handle is formed of a plurality of threadably interconnected pipe segments.

10. The capacitance sensing probe of claim 1 wherein said electronic circuit comprises:
a circuit board;
a first electrical connection wire interconnecting said first electrode and said circuit board; and
a second electrical connection wire interconnecting said second electrode and said circuit board.

11. The capacitance sensing probe of claim 10 further comprising:
a coaxial cable connected to said circuit board and extending beyond said internal cavity to the exterior of said probe body; and
a ferrite shield carried by said coaxial cable adjacent said probe body to substantially reduce undesirable signal interference.

12. The capacitance sensing probe of claim 1 wherein said internal cavity is back-filled with dielectric filler to prevent moisture damage to said circuit.

13. A capacitance sensing probe for measuring the moisture content of soil through an access tube embedded in the soil, said probe having a generally cylindrical probe body with first and second opposite ends, said generally cylindrical probe body comprising:
first and second substantially rigid structural components having the form of right circular cylinders and defining, respectively, first and second electrically conductive capacitance sensing electrodes, said first electrode being located at said first end of said generally cylindrical probe body;
a dielectric spacer having the form of a right circular cylinder and being securely attached to each of said first and second electrodes such that said electrodes are dielectrically and longitudinally spaced apart at opposite ends of said spacer;
an internal cavity formed within at least said second one of said electrodes;
an electronic circuit located within said internal cavity and electrically connected to each of said first and second electrodes;
a dielectric filler filling said internal cavity to prevent moisture damage to said circuit;
a threaded end cap mounted on said second end of said probe body and having a diameter less than that of said probe body;
a dielectric material in the form of a right circular cylinder interposed between said threaded end cap and said second electrode;
at least three equidistant and circumferentially spaced apart spring biased plungers located in the proximity of said first end of said probe body and extending radially outwardly from said probe body for engaging the side wall of the access tube and centering said probe body within the tube; and
at least three equidistant and circumferentially spaced apart spring biased plungers located in the proximity of said second end of said probe body and extending radially outwardly from said probe body for engaging the side wall of the access tube and centering said probe body within the tube;
said capacitance sensing probe further comprising an elongate tubular handle having at one end thereof a threaded portion corresponding to said threaded end cap of said probe body, said handle being threadedly engaged with said end cap to facilitate axially moving said probe body within the access tube.

14. A capacitance monitor for monitoring soil moisture, said capacitance monitor comprising an access tube extending into the soil and having an upper end portion that projects above the level of the soil, a top cap assembly mounted on the extreme upper end portion of said access tube, and a capacitance sensing probe having a generally cylindrical probe body for measuring the moisture content of the soil, said capacitance sensing probe also having an elongate tubular handle mounted on said probe body to facilitate axially moving said probe body within said access tube, said generally cylindrical probe body comprising:
first and second substantially rigid structural components defining, respectively, first and second electrically conductive capacitance sensing electrodes;
a dielectric spacer securely attached to each of said first and second structural components such that said components are dielectrically and longitudinally spaced apart at opposite ends of said spacer;
an internal cavity formed within at least one of said structural components;
an electronic circuit located within said internal cavity and electrically connected to each of said first and second electrodes;
a first circumferentially spaced apart plurality of means extending radially outwardly from said probe body for engaging the side wall of said access tube and centering said probe body within said tube; and
a second circumferentially spaced apart plurality of means extending radially outwardly from said probe body for engaging the side wall of said access tube and centering said probe body within said tube; said second means being longitudinally spaced from said first means.

15. The capacitance monitor of claim 14 wherein said top cap assembly comprises:
a sleeve fitted over said extreme upper end portion said access tube, said sleeve including circumferentially spaced means for fixing said sleeve to said access tube;
a cover plate fixed to said sleeve defining an aperture for receiving said capacitance sensing probe, said aperture having beveled side walls for engaging said first and second means on said probe body and urging said means radially inwardly so that said probe body can be inserted into said access tube; and
stop assembly means mounted to said cover plate for engaging said tubular handle to control reproducibly positioning said probe body at predetermined depths within said access tube.

16. The capacitance monitor of claim 15 wherein said tubular handle includes surfaces for engaging said stop assembly means at predetermined intervals along its length.

17. The monitor of claim 16 wherein said tubular handle is of smaller diameter than said probe body and said top cap assembly further comprises a hinge plate hingeably mounted to said cover plate for reducing the size of said aperture when said probe body is in said access tube and said smaller diameter handle extends through said aperture for engagement with said stop means.

18. The capacitance monitor of claim 14 wherein said probe body further comprises a threaded end cap and said tubular handle is mounted to said threaded end cap through a corresponding threaded end portion.

19. The capacitance monitor of claim 18 wherein said probe body further comprises a right circular cylindrical dielectric material interposed between said threaded end cap and one of said electrodes.

20. The capacitance monitor of claim 14 wherein said electronic circuit further comprises:
a circuit board;
a first electrical connection wire interconnecting said first electrode and said circuit board; and
a second electrical connection wire interconnecting said second electrode and said circuit board; and wherein said capacitance monitor further comprises:
a coaxial cable having first and second opposite ends, said first end thereof being connected to said circuit board, and said second end thereof extending beyond said internal cavity to the exterior of said probe body; and
a control box connected to said coaxial cable at said second end of said coaxial cable, said control box correlating the capacitance of the soil to the moisture content of the soil.

21. The capacitance monitor of claim 20 further comprising a ferrite shield carried by said coaxial cable adjacent said probe body to substantially reduce undesirable signal interference.

22. The capacitance monitor of claim 14 wherein said first and second electrodes are right circular cylinders and are formed of aluminum, and wherein said dielectric spacer is also a right circular cylinder, and is formed of polypropylene.

23. The capacitance monitor probe of claim 14 wherein said internal cavity is back-filled with dielectric filler to prevent moisture damage to said circuit.

24. The capacitance monitor of claim 15 wherein said stop assembly further comprises a spring biased stop pin mounted for engagement with said tubular handle at predetermined intervals to control reproducibly positioning said probe body at predetermined depths within said access tube.

25. A capacitance monitor for monitoring soil moisture comprising:
an access tube embedded in the soil;
a capacitance sensing probe adapted to be inserted into said access tube, said capacitance sensing probe comprising:
a generally cylindrical probe body with first and second opposite ends, said generally cylindrical probe body comprising:
first and second substantially rigid structural components having the form of right circular cylinders and defining, respectively, first and second electrically conductive capacitance sensing electrodes, said first electrode being located at said first end of said generally cylindrical probe body;
a dielectric spacer having the form of a right circular cylinder and being securely attached to each of said first and second electrodes such that said electrodes are dielectrically and longitudinally spaced apart at opposite ends of said spacer;
an internal cavity formed within at least said second one of said electrodes;
an electronic circuit located within said internal cavity and electrically connected to each of said first and second electrodes;
a dielectric filler filling said internal cavity to prevent moisture damage to said circuit;
a threaded end cap mounted on said second end of said probe body;
a dielectric material in the form of a right circular cylinder interposed between said threaded end cap and said second electrode;
at least three equidistant and circumferentially spaced apart spring biased plungers located in the proximity of said first end of said probe body and extending radially outwardly from said probe body for engaging the side wall of said access tube and centering said probe body within said tube; and
at least three equidistance and circumferentially spaced apart spring biased plungers located in the proximity of said second end of said probe body and extending radially outwardly from said probe body for engaging the side wall of said access tube and centering said probe body within said tube; said capacitance sensing probe further comprising:
an elongate tubular handle having at one end thereof a threaded portion corresponding to said threaded end cap, said handle being threadedly engaged with said end cap to facilitate axially moving said probe body within said access tube; and
said capacitance monitor further comprising:
a top cap assembly mounted on the extreme upper end portion of said access tube and comprising:
a sleeve fitted over said extreme upper end portion said access tube, said sleeve including circumferentially spaced means for fixing said sleeve to said access tube;

a cover plate fixed to said sleeve defining an aperture for receiving said capacitance sensing probe, said aperture having beveled side walls for engaging said first and second means on said probe body and urging said means radially inwardly so that said probe body can be inserted into said access tube; and stop assembly means mounted to said cover plate for engaging said tubular handle to control reproducibly positioning said probe body at predetermined depths within said access tube.

26. A capacitance sensing probe for measuring the moisture content of soil through an access tube embedded in the soil, said capacitance sensing probe having a generally cylindrical body comprising:

first and second substantially rigid structural components defining, respectively, first and second electrically conductive capacitance sensing electrodes;

a dielectric spacer securely attached to each of said first and second structural components such that said components are dielectrically and longitudinally spaced apart at opposite ends of said spacer;

an internal cavity formed within at least one of said structural components;

an electronic circuit located within said internal cavity and electrically connected to each of said first and second electrodes;

a first circumferentially spaced apart plurality of means extending radially outwardly from said probe body for engaging the side wall of the access tube and centering said probe body within the tube; and a second circumferentially spaced apart plurality of means extending radially outwardly from said probe body for engaging the side wall of the access tube and centering said probe body within the tube, said second means being longitudinally spaced from said first means;

said capacitance sensing probe further comprising an elongate tubular handle having at one end thereof a threaded portion corresponding to said threaded end cap of said probe body, said handle being threadedly engaged with said end cap to facilitate axially moving said probe body within the access tube.

27. The capacitance sensing probe of claim 26 wherein said handle is of smaller diameter than said probe body and is formed from PVC pipe.

28. A capacitance sensing probe for measuring the moisture content of soil through an access tube embedded in the soil, said capacitance sensing probe having a generally cylindrical body comprising:

first and second substantially rigid structural components defining, respectively, first and second electrically conductive capacitance sensing electrodes;

a dielectric spacer securely attached to each of said first and second structural components such that said components are dielectrically and longitudinally spaced apart at opposite ends of said spacer;

an internal cavity formed within at least one of said structural components;

an electronic circuit located within said internal cavity and electrically connected to each of said first and second electrodes;

a first circumferentially spaced apart plurality of means extending radially outwardly from said probe body for engaging the side wall of the access tube and centering said probe body within the tube; and a second circumferentially spaced apart plurality of means extending radially outwardly from said probe body for engaging the side wall of the access tube and centering said probe body within the tube, said second means being longitudinally spaced from said first means;

said capacitance sensing probe further comprising an elongate tubular handle formed of a plurality of threadably interconnected pipe segments and means for mounting said handle to one end of said cylindrical probe body to facilitate axially moving said probe body within the access tube.

* * * * *

UNITED STATES PATENT AND TRADEMARK OFFICE
CERTIFICATE OF CORRECTION

PATENT NO. : 5,260,666

DATED : November 9, 1993

INVENTOR(S) : Michael R. Dishman et al

It is certified that error appears in the above-identified patent and that said Letters Patent is hereby corrected as shown below:

On the cover page, under References Cited, please insert
-- Dean, T.J. et al., Soil Moisture Measurement By
An Improved Capacitance Technique, Part I. Sensor
Design And Performance, 1987, pp. 67-90. --.

Signed and Sealed this

Twenty-sixth Day of April, 1994

Attest:

BRUCE LEHMAN

*Attesting Officer*  *Commissioner of Patents and Trademarks*